United States Patent
Willoughby et al.

(10) Patent No.: US 10,143,803 B2
(45) Date of Patent: Dec. 4, 2018

(54) MEDICAMENT DELIVERY DEVICE SUB-ASSEMBLY

(71) Applicant: CONSORT MEDICAL PLC, Hemel Hempstead (GB)

(72) Inventors: Alastair Willoughby, Cambridge (GB); Marta Vilaplana, Cambridge (GB)

(73) Assignee: CONSORT MEDICAL PLC, Hemel Hempstead (GB)

( * ) Notice: Subject to any disclaimer, the term of this patent is extended or adjusted under 35 U.S.C. 154(b) by 396 days.

(21) Appl. No.: 15/032,994

(22) PCT Filed: Nov. 3, 2014

(86) PCT No.: PCT/GB2014/053250
§ 371 (c)(1),
(2) Date: Apr. 28, 2016

(87) PCT Pub. No.: WO2015/063506
PCT Pub. Date: May 7, 2015

(65) Prior Publication Data
US 2016/0287790 A1    Oct. 6, 2016

(30) Foreign Application Priority Data

Nov. 1, 2013   (GB) .................................. 1319380.0

(51) Int. Cl.
*A61M 5/20*   (2006.01)
*A61M 5/24*   (2006.01)
*A61M 5/145*   (2006.01)

(52) U.S. Cl.
CPC ........ *A61M 5/2053* (2013.01); *A61M 5/2046* (2013.01); *A61M 2005/14513* (2013.01);
(Continued)

(58) Field of Classification Search
CPC .............. A61M 5/315; A61M 5/31501; A61M 5/31513; A61M 5/31515; A61M 5/31511;
(Continued)

(56) References Cited

U.S. PATENT DOCUMENTS 2,895,474 A * 7/1959 Reznek .................... A61M 5/24
604/228
4,861,340 A * 8/1989 Smith ................. A61M 5/2053
604/141

(Continued)

FOREIGN PATENT DOCUMENTS

WO   WO2005070483 A1   8/2005
WO   WO2014066461 A1   5/2014

OTHER PUBLICATIONS

Patent Cooperation Treaty, International Searching Authority, "Notification of Transmittal of the ISR and the Written Opinion of the International Search Authority, or the Declaration"; dated Jan. 26, 2015; 5 pages.

(Continued)

*Primary Examiner* — Scott J Medway
*Assistant Examiner* — Justin L Zamory
(74) *Attorney, Agent, or Firm* — Taft Stetinius & Hollister LLP; Stephen F. Rost (57) ABSTRACT

A sub-assembly of a medicament delivery device, the sub-assembly including a propellant source having a reservoir housing defining a reservoir and a stem having a bore therethrough, at least one inlet in fluid communication with the bore, and an open outlet end in fluid communication with the bore, the stein being moveable relative to the reservoir housing between a first position in which the at least one inlet is not in fluid communication with the reservoir and a second position in which the at least one inlet is in fluid communication with the reservoir, the propellant source further including a biasing member for biasing the stem (Continued)

towards the first position. The sub-assembly further including a collet member having a first plurality of radially flexible fingers and a second plurality of radially flexible fingers.

18 Claims, 8 Drawing Sheets

(52) U.S. Cl.
CPC ............... *A61M 2005/2073* (2013.01); *A61M 2005/244* (2013.01); *A61M 2205/3334* (2013.01); *A61M 2205/8225* (2013.01)

(58) Field of Classification Search
CPC ............ A61M 5/31581; A61M 5/2429; A61M 5/5086; A61M 2005/2073; A61M 2005/244; B32B 31/202; Y10T 408/953
See application file for complete search history.

(56) References Cited

U.S. PATENT DOCUMENTS

| | | | |
|---|---|---|---|
| 5,330,501 A | * | 7/1994 | Tovey ................ A61B 17/3421 604/105 |
| 2002/0188251 A1 | | 12/2002 | Staylor et al. |
| 2008/0058719 A1 | | 3/2008 | Edwards et al. |
| 2012/0041426 A1 | * | 2/2012 | Bizup ................ A61M 39/1011 604/536 |

OTHER PUBLICATIONS

PCT Written Opinion of the ISA, dated Jan. 26, 2015, 6 pages.
Combined Search and Examination report under Section 17 and 18(3); Intellectual Property Office, 5 pages.

\* cited by examiner

MEDICAMENT DELIVERY DEVICE SUB-ASSEMBLY

This application is a U.S national stage application under 35 U.S.C. § 371 of PCT International Application Serial No. PCT/GB2014/053250, which has an international filing date of Nov. 3, 2014 designates the United States of America, and claims the benefit of GB Application No. 1319380.0, which was filed on Nov. 1, 2013. The disclosures of each of these prior applications are hereby expressly incorporated by reference in their entirety.

This invention relates to a medicament delivery device, and in particular, to a sub-assembly of a medicament delivery device for receiving a syringe.

BACKGROUND

Known medicament delivery devices include autoinjector devices and in certain instances consist of a sub-assembly and a syringe that is installed in the sub-assembly. Some of these prior art arrangements have the advantage of permitting the use of standard specification syringes in a delivery device irrespective of the syringe manufacturer, thereby obviating the need for pharmaceutical companies to provide filled syringes specific to a particular device.

It is an object of at least one embodiment of the present invention to provide a sub-assembly for a medicament delivery device that overcomes at least some of the disadvantages associated with prior art arrangements.

BRIEF SUMMARY OF THE DISCLOSURE

In accordance with a first aspect of the present invention, there is provided a sub-assembly of a medicament delivery device, the sub-assembly comprising:
  a propellant source comprising a reservoir housing defining a reservoir and a stem having a bore therethrough, at least one inlet in fluid communication with the bore, and an open outlet end in fluid communication with the bore, the stem being moveable relative to the reservoir housing between a first position in which the at least one inlet is not in fluid communication with the reservoir and a second position in which the at least one inlet is in fluid communication with the reservoir, the propellant source further comprising a biasing member for biasing the stem towards the first position; and
  a collet member having a first plurality of radially flexible fingers and a second plurality of radially flexible fingers wherein the first plurality of radially flexible fingers extend radially inwards of the second plurality of radially flexible fingers when each of said first and second plurality of radially flexible fingers are unbiased;
  wherein the first plurality of radially flexible fingers are configured to engage the stem so as to inhibit axial movement of the stem relative to the collet member when the stem is urged in an axial direction with a force less than a force threshold but permit axial movement of the stem relative to the collet member when the stem is urged in an axial direction with a force greater than or equal to the force threshold, and the second plurality of radially flexible fingers do not prevent axial movement of the stem relative to the collet member when in a radially outward position but engage the stem when in a biased radially inward position so as to inhibit axial movement of the stem relative to the collet member including when the stem is urged in an axial direction with a force that is substantially equal to or greater than the force threshold and that is substantially equal to or greater than the force required to compress the biasing member and permit the stem to move to the second position relative to the reservoir housing, wherein the force threshold is substantially equal to or less than the force required to compress the biasing member.

The first plurality of radially flexible fingers and the second plurality of radially flexible fingers may be circularly arranged relative to one another, where the first plurality of radially flexible fingers and the second plurality of radially flexible fingers may be alternately arranged in the circular arrangement.

The first plurality of radially flexible fingers may comprise three radially flexible fingers and the second plurality of radially flexible fingers may comprise three radially flexible fingers.

Each of the first plurality of radially flexible fingers and second plurality of radially flexible fingers may include a radially inwardly directed lug for engaging the stem, wherein the lugs on each of the first plurality of radially flexible fingers may be tapered in an axial direction. The stem may include a circumferential groove in an outer surface of the stem, and the lugs of the first plurality of radially flexible fingers and the second plurality of radially flexible fingers may be engageable in said groove, such that the presence of the lugs in the groove axially blocks a part of the stem.

The propellant source may include a latching mechanism that is configured to latch the stem in the second position. The latching mechanism may include latching members that are arranged to permit axially rearwardly movement of the stem relative to the reservoir housing, but substantially prevent forwardly axial movement of the stem relative to the reservoir housing when the stem is displaced relative to the reservoir housing by a predetermined distance. The stem may include a stem flange extending radially outwardly from the stem inside the reservoir housing, and wherein the predetermined distance is the distance required to position the stem flange axially rearwardly of the latching members such that abutment of the stem flange by the latching members prevents forwardly axial movement of the stem relative to the reservoir housing.

The sub-assembly may further comprise an O-ring seal circumventing the stem at an axial position that is forward of the first plurality of radially flexible fingers and the second plurality of radially flexible fingers, wherein the O-ring seal is configured to form a seal between the stem and a syringe barrel when a syringe is installed on the sub-assembly. The sub-assembly may further comprise a retainer member axially forwardly of the O-ring seal and configured to axially restrain the O-ring seal on the stem between the retainer member and the first plurality of radially flexible fingers and the second plurality of radially flexible fingers.

The sub-assembly may further comprise a front housing attached to the collet member. The sub-assembly may further comprise a button that is axially moveable relative to the collet member, wherein axially forwardly movement of the button causes an axially forwardly force to be applied to the propellant container.

The reservoir may contain a liquefied gas propellant and/or the reservoir may contain a propellant that is or contains a hydrofluoroalkane (HFA), wherein the propellant may be or contain HFA134a.

In accordance with one aspect of the present invention, there is provided a medicament delivery device comprising a sub-assembly according to the first aspect of the present invention and a syringe installed in the sub-assembly, the syringe comprising a barrel, a stopper axially moveable in the barrel and an outlet at a front end of the barrel, wherein the barrel biases the second plurality of radially flexible fingers to the biased radially inward position so as to inhibit axial movement of the stem relative to the collet member.

In accordance with a second aspect of the present invention, there is provided a sub-assembly of a medicament delivery device, the sub-assembly comprising:
  a housing for containing a propellant source, the housing being configured to receive a flange of a syringe; and
  a locking ring for attachment to the housing;
  wherein the locking ring is configured to retain a syringe flange received in the housing between the locking ring and the housing when the locking ring is attached to the housing.

The housing may include a non-circular aperture for receiving a flange of a syringe, wherein the non-circular aperture has a narrow dimension that is less than a maximum dimension of the non-circular aperture, the narrow dimension being configured to prevent forward axial movement of a syringe flange disposed axially rearward of the narrow dimension, wherein the syringe flange has a maximum diameter that is greater than the narrow dimension. The narrow dimension of the non-circular aperture may be defined by a pair of diametrically opposed side walls. The sub-assembly according may further comprise one or more biasing members for biasing a syringe flange axially forwardly against the housing either side of the narrow dimension. The one or more biasing members may comprise one or more leaf springs, and/or may form part of the housing. The housing may include a collet member, and the one or more biasing members form part of the collet member.

The locking ring may include at least one pair of clips for engaging in a pair of sockets of the housing and attaching the locking ring to the housing. At least one of the clips may limit rotation of a syringe flange about a longitudinal axis of the sub-assembly when engaged in the respective socket.

The housing may include one or more stops for limiting rotation of a syringe flange about a longitudinal axis of the sub-assembly. The at least one clip and the one or more stops may be circumferentially spaced from one another so as to substantially prevent both clockwise and anticlockwise rotation about a longitudinal axis of the sub-assembly of a syringe flange disposed between the at least one clip and the one or more stops.

The sub-assembly may further comprise a propellant source disposed in the housing, wherein the propellant source includes a reservoir containing a propellant. The reservoir may contain a liquefied gas propellant, and/or may contain a propellant that is or contains a hydrofluoroalkane (HFA), and may be or contain HFA134a.

In accordance with an aspect of the present invention, there is provided a medicament delivery device comprising a sub-assembly according to the second aspect of the present invention and a syringe, the syringe comprising a barrel, a stopper axially moveable in the barrel, a syringe flange extending radially outward from a rear end of the barrel, and an outlet at a front end of the barrel, wherein the locking ring is attached to the housing and the syringe flange is retained in the housing between the locking ring and the housing.

In accordance with a third aspect of the present invention, there is provided a sub-assembly of a medicament delivery device comprising:
  a propellant source having a reservoir for containing a propellant and a stem for dispensing propellant from the reservoir, the stem extending axially along a longitudinal axis and having an open outlet end and a bore therethrough that is in fluid communication with said open outlet end and is selectively in fluid communication with said reservoir; and
  a spray head member attachable to the stem;
  wherein the spray head member is arranged to radially deflect propellant passing through the bore and out of the open outlet of the stem relative to the longitudinal axis.

The spray head member may be attachable to an external surface of the stem. Alternatively, the spray head member may be attachable in the bore of the stem, optionally by a frictional engagement between the spray head member and a surface defining the bore.

The spray head member may include a spigot for extending into the bore and a deflection portion for providing a radial component to the flow path of propellant exiting the open outlet end of the stem. The spigot may comprise a plurality of circumferentially spaced limbs projecting radially outwardly from a central longitudinal axis of the spray head member, wherein circumferential spaces between limbs form channels providing a fluid pathway from the bore through the open outlet end. The circumferentially spaced limbs may comprise four limbs each arranged orthogonally to an adjacent limb. A rear end of the spigot may taper radially inwardly in an axially rearward direction for facilitating locating of the spigot in the bore. The spray head member may be a retainer member and further comprises a portion extending radially outwardly from the spigot beyond the outer radius of the stem. The portion extending radially outwardly from the spigot may comprise a retainer flange that is circumferentially continuous. The retainer flange may be the deflection portion.

The sub-assembly may further comprise a continuous seal extending around an external perimeter surface of the stem for sealing the stem to an inside surface of a syringe barrel, wherein the continuous seal is axially restrained by portion extending radially outwardly from the spigot beyond the outer radius of the stem. The sub-assembly may further comprise a housing, wherein the continuous seal is axially restrained between the housing and the portion extending radially outwardly from the spigot beyond the outer radius of the stem. The housing may include a collet member, and the continuous seal is axially restrained between the collet member and the portion extending radially outwardly from the spigot beyond the outer radius of the stem.

The sub-assembly may further comprise one or more spacer elements extending radially from the spigot beyond the radius of the bore such that the one or more spacer elements limit the axial depth to which the spigot may be inserted into the bore. The one or more spacer elements may comprise circumferentially spaced spacer elements. The circumferentially spaced spacer elements may comprise four spacer elements each arranged orthogonally to an adjacent spacer element.

The spray head member may be arranged to deflect axially flowing propellant in the bore by at least 45 relative to the longitudinal axis.

In accordance with a fourth aspect of the present invention, there is provided a sub-assembly of a medicament delivery device comprising:
  a propellant source having a reservoir for containing a propellant and a stem for dispensing propellant from the reservoir, the stem having an open outlet end and a bore therethrough that is in fluid communication with said open outlet end and is selectively in fluid communication with said reservoir;

a continuous seal extending around an external perimeter surface of the stem; and a retainer member having a spigot extending into the bore of the stem through the open outlet end, a portion extending radially outwardly from the spigot beyond the outer radius of the stem, and one or more channels providing a fluid pathway from the bore through the open outlet end.

The continuous seal may be an O-ring seal.

The spigot may comprise a plurality of circumferentially spaced limbs projecting radially outwardly from a central longitudinal axis of the retainer member, wherein circumferential spaces between limbs form the one or more channels. The circumferentially spaced limbs may comprise four limbs each arranged orthogonally to an adjacent limb. The spigot may form a frictional fit inside the bore of the stem. A rear end of the spigot may taper radially inwardly in an axially rearward direction for facilitating locating of the spigot in the bore. The portion extending radially outwardly from the spigot may comprise a retainer flange that is circumferentially continuous. The sub-assembly may further comprise one or more spacer elements extending radially from the spigot beyond the radius of the bore such that the one or more spacer elements limit the axial depth to which the spigot may be inserted into the bore. The one or more spacer elements may comprise circumferentially spaced spacer elements. The circumferentially spaced spacer elements may comprise four spacer elements each arranged orthogonally to an adjacent spacer element. The channels may be partly defined by the circumferential spaces between the one or more spacer elements and a rear surface of the retainer flange. The channels may pass through the portion of the retainer member extending radially outwardly from the spigot.

The sub-assembly may further comprise a housing, wherein the continuous seal is axially restrained between the retainer member and the housing. The housing may include a collet member, and the continuous seal is axially restrained between the retainer member and the collet member.

The reservoir may contain a liquefied gas propellant, and/or the reservoir may contain a propellant that is or contains a hydrofluoroalkane (HFA), and may be or contain HFA134a In accordance with one aspect of the present invention, there is provided a medicament delivery device comprising a sub-assembly according to the third or fourth aspects of the invention and a syringe installed in the sub-assembly, the syringe comprising a barrel, a stopper axially moveable in the barrel and an outlet at a front end of the barrel.

Certain embodiments of the present invention may include any suitable combination of features any of the first, second, third and fourth aspects of the present invention.

BRIEF DESCRIPTION OF THE DRAWINGS

Embodiments of the invention are further described hereinafter with reference to the accompanying drawings, in which.

DETAILED DESCRIPTION

Figure 1:
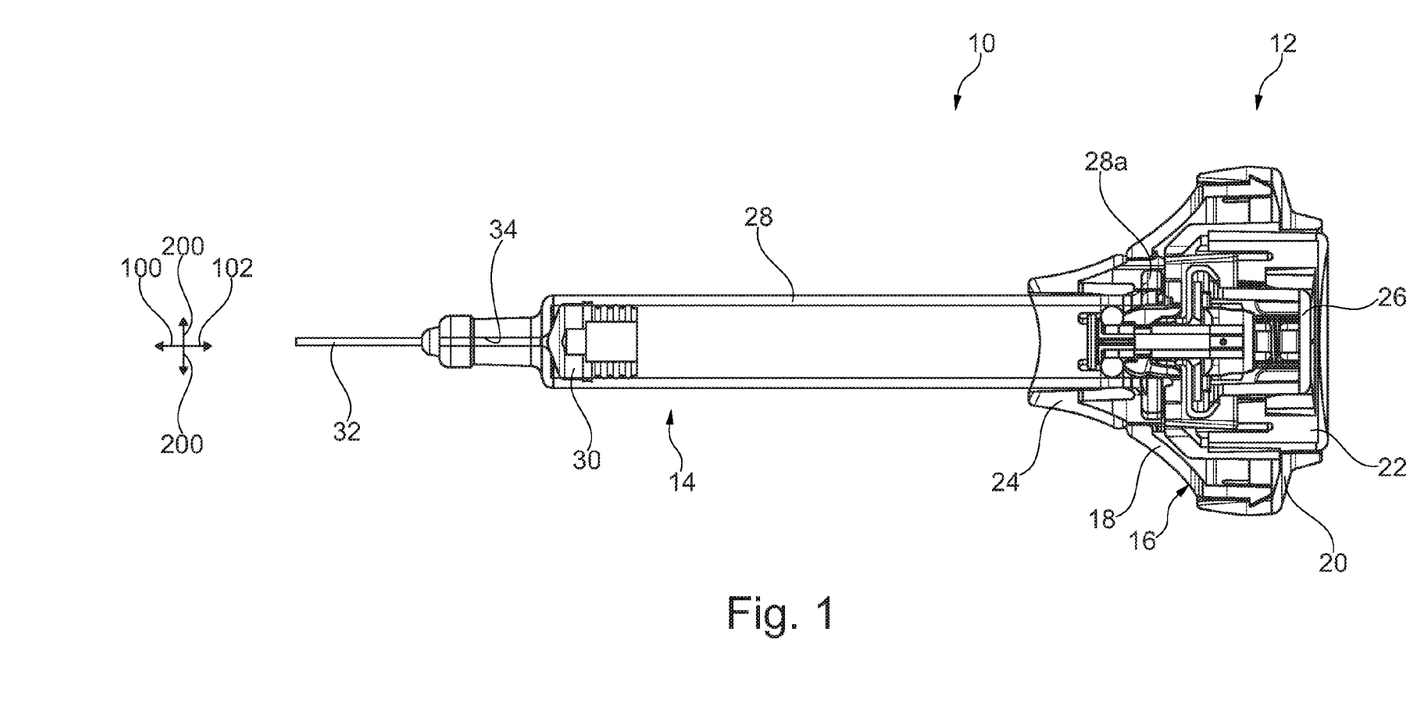
FIG. 1 is a cross-sectional view of a medicament delivery device.

FIG. 1 shows a cross-sectional view of a medicament delivery device 10 that includes a sub-assembly 12 and a syringe 14 retained by the sub-assembly 12. The syringe 14 has a syringe barrel 28 having a flange 28*a* at a rear end, a stopper 30 disposed in the syringe barrel 28 and axially slidable therein, and a needle 32 in fluid communication with a fluid outlet 34 of the syringe 14. The syringe 14 is configured to contain a medicament and permit delivery of the medicament to a delivery site when the stopper 30 moves axially forwardly in the syringe barrel 28 and causes medicament to be expelled through the needle 32 via the fluid outlet 34.

The device 10 extends in an axial direction along a longitudinal axis. The forward axial direction is indicated by arrow 100 in FIG. 1 and the rearward axial direction is indicated by arrow 102. Radial directions are indicated by arrows 200 and are relative to the longitudinal axis (i.e. the axial line through the centre of the device)

The sub-assembly 12 includes a housing 16 that is formed by a front housing 18 and a collet member 20. In the embodiment shown in FIG. 1, the sub-assembly 12 further includes a button 22 and a locking ring 24. The sub-assembly 12 also includes a propellant source 26 for supplying a propellant that may provide a vapour pressure that is sufficient to cause axial movement of the stopper 30 of the syringe 14 and deliver a dose of medicament.

The propellant may be any propellant that is suitable for providing a vapour pressure to the syringe 14. In preferable embodiments, the propellant is a liquefied gas that vaporizes to provide a vapour pressure. In particularly preferable embodiments, the propellant may be or contain a hydrofluoroalkane (HFA), and specifically may be or contain HFA 134a.

The housing 16 is configured to receive the flange 28*a* of the syringe 14 and the locking ring 24 attaches to the housing 16 such that the flange 28*a* received in the housing 16 is retained between the locking ring 24 and the housing 16. A specific embodiment of an attachment mechanism between the syringe 14 and the housing 16 is shown in FIG. 2.

Figure 2:
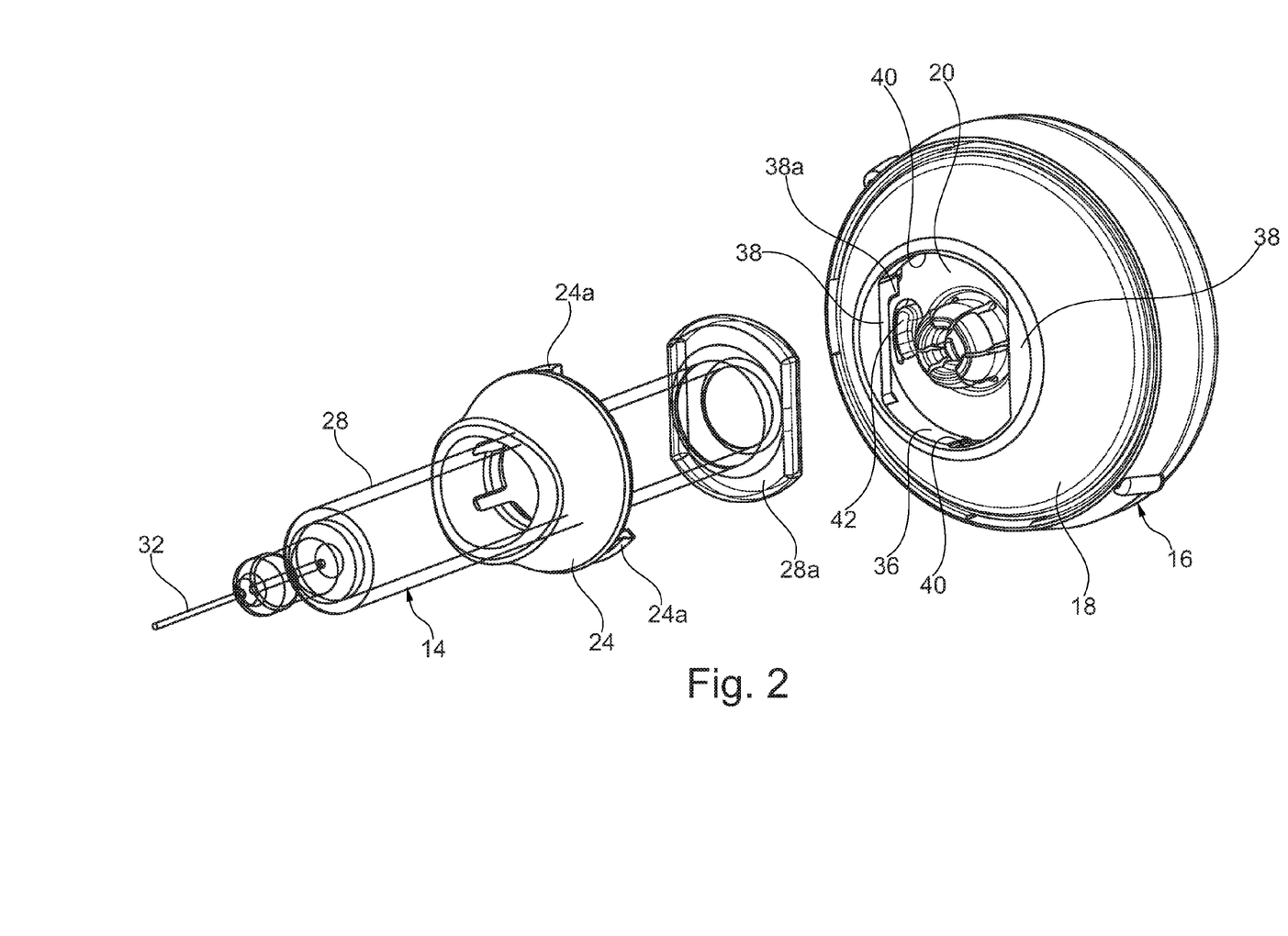
FIG. 2 is an exploded perspective view of a syringe and part of a sub-assembly of a medicament delivery device.

From FIG. 2, it can be seen that the flange 28*a* of the syringe 14 has a varying radial extent about its circumference. That is, the flange 28*a* extends radially further in some parts compared with others (i.e. the flange 28*a* has a non-circular profile). The front housing 18 has an aperture 36 that has a profile corresponding to the shape of the flange 28*a*, but larger so as to permit insertion of the flange 28*a* therein. The aperture 36 is partly defined by diametrically opposed side walls 38 that are spaced apart by a distance that is less than the maximum diametric distance of the aperture 36. During assembly, the flange 28*a* is inserted into the aperture 36 and then rotated about the longitudinal axis so that the more radially outward parts of the flange 28*a* are axially aligned with and axially rearward of the side walls 38. In such a position, the side walls 38 prevent forward axial movement of the syringe 14 relative to the housing. In the preferable embodiment shown in FIG. 2, the side walls 38 include stops 38a which are arranged to abut the syringe flange 28a and thereby limit rotation of the syringe flange 28a about the longitudinal axis relative to the front housing 18. The housing 16 includes one or more biasing members 42 for biasing the syringe flange 28a axially forwardly against a rear side of the side walls 38. In the preferable embodiment shown in FIG. 2, the biasing members 42 are a pair of leaf springs formed in the collet member 20. The locking ring 24 attaches to the front housing 18 and retains the received syringe flange 28a between the locking ring 24 and the collet member 20 (with a part of the front housing 18 being axially disposed between the flange 28a and the locking ring 24). In particular, the locking ring 24 has an inner diameter that is less than the greatest diameter of the flange 28a such that the flange 28a cannot pass through the locking ring 24. Additionally, the locking ring 24 includes clips 24a that locate in and engage with sockets 40 on the front housing 18. The presence of the clips 24a engaged in the sockets 40 limits rotation of the retained syringe flange 28a about the longitudinal axis such that when the locking ring 24 is attached to the front housing 18, the syringe flange 28a cannot rotate to a configuration that permits the release of the syringe flange 28a from the aperture 36.

Figure 3:
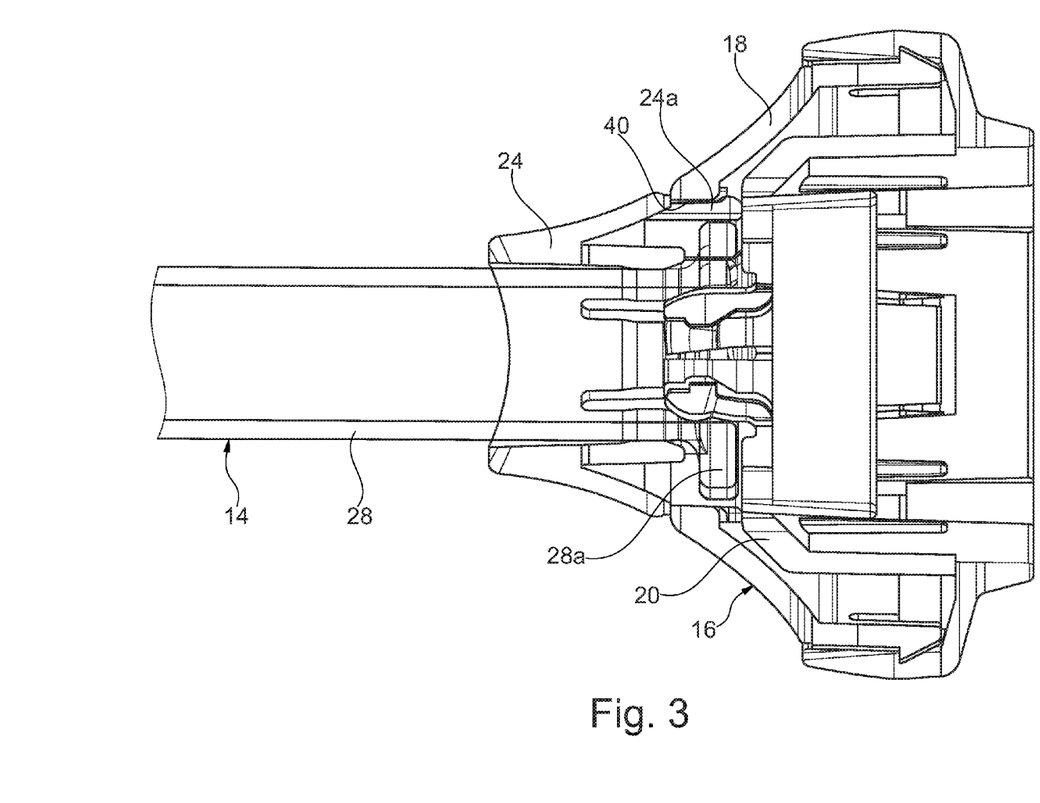
FIG. 3 is a cross-sectional view of a syringe and part of a sub-assembly of a medicament delivery device.

FIG. 3 shows a cross-sectional view of a syringe flange 28a retained in the housing 16 corresponding to the embodiment described above in relation to FIG. 2.

The attachment mechanism described above in relation to FIGS. 2 and 3 permits connection between the housing 16 and the syringe 14 and can accommodate the clearance and tolerance of different syringe designs. Thus, a connection mechanism is provided that can permit the attachment of a wide variety of syringes to the housing 16 of the sub-assembly 12.

Figure 4:
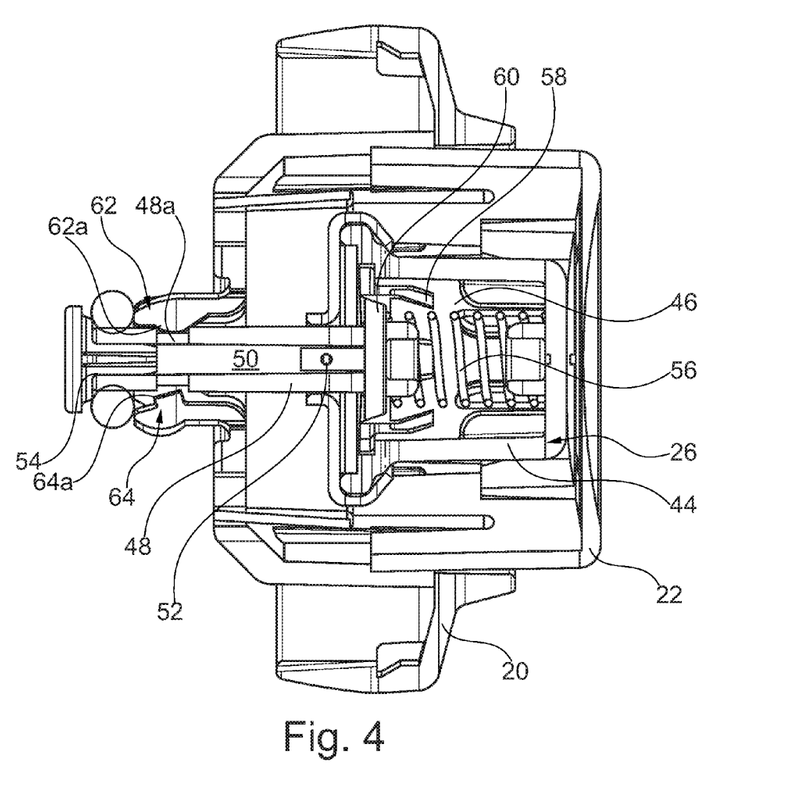
FIG. 4 is a cross-sectional view of part of a sub-assembly including a propellant source.
Figure 5:
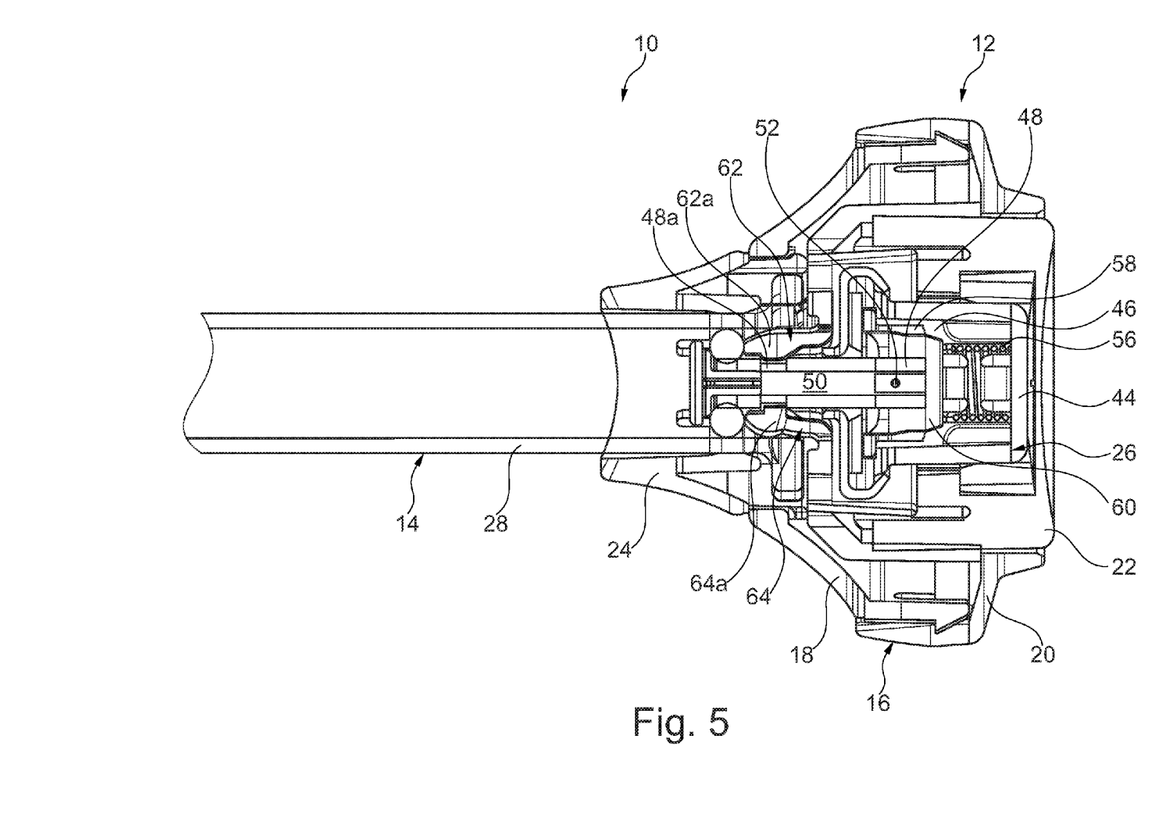
FIG. 5 is a cross-sectional view of the sub-assembly of FIG. 4 with a syringe installed.

FIGS. 4 and 5 show cross-sectional views of a connection mechanism between the propellant source 26 and the collet member 20. FIG. 4 shows the collet member 20, propellant source 26 and button 22 without the front housing 18 assembled thereon and prior to assembly of the syringe 14 and locking ring 24. The propellant source 26 comprises a reservoir housing 44 that defines a reservoir 46 for containing a propellant, and a stem 48. The stem 48 has a bore 50 therethrough, an inlet 52 in fluid communication with the bore 50 and an open outlet end 54 also in fluid communication with the bore 50. Additionally, the stem 48 has a groove 48a circumventing its outer surface towards a front end of the stem 48.

The stem 48 is axially moveable relative to the reservoir housing 44 between a first position (as shown in FIG. 4) in which the inlet 52 is not in fluid communication with the reservoir 46 and a second position (as shown in FIG. 5) in which the inlet 52 is in fluid communication with the reservoir 46. The propellant source 26 additionally includes a biasing member 56, which, in the embodiment shown in the Figures, is a spring, that biases the stem 48 towards the first position. In particular, the stem 48 includes a stem flange 60 that the biasing member 56 acts upon. The propellant source 26 optionally has latching members 58 that are radially flexible and project axially rearwardly and radially inwardly such that, in a relaxed state, the latching members 58 are partly radially inward of the radially outermost parts of the stem flange 60. In use, reservoir housing 44 is moved axially forwardly relative to the stem 48, compressing biasing member 56 and causing the latching members 58 to flex radially outwardly due to a camming action caused by the stem flange 60 moving axially rearwardly relative thereto. Once the stem flange 60 is axially rearward of the latching members 58, the latching members 58 relax once more to a position that is partly radially inward of the radially outermost parts of the stem flange 60. Due to the profile of the latching members 60, subsequent forwardly axial movement of the stem flange 60 relative to the reservoir housing does not cause the latching members 58 to flex radially outwardly, and, instead, the latching members 58 abut the stem flange 60 and prevent further forwardly axial movement. Thus, relative rearward axial movement of the stem flange 60 beyond the latching members 58 causes the stem 48 to become latched in the second position.

The button 22 provides a user-friendly surface for applying an axially forwardly force to the propellant container 26.

Figure 6:
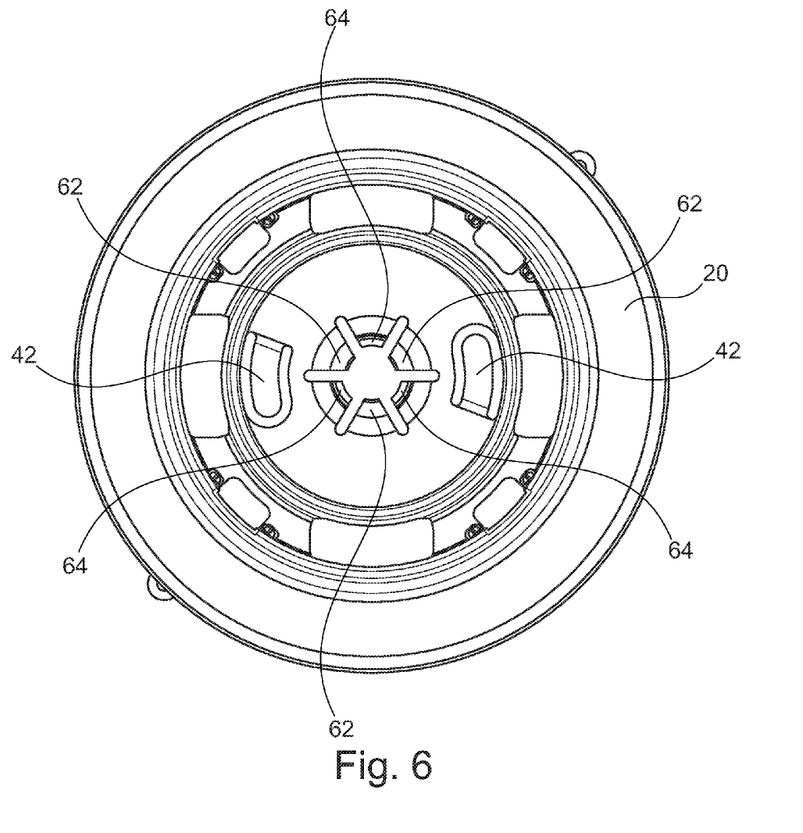
FIG. 6 is an axial rear view of the collet member of the sub-assembly of FIGS. 4 and 5.

The collet member 20 includes a first plurality of radially flexible fingers 62 and a second plurality of radially flexible fingers 64 arranged generally in a circular configuration. In a relaxed (i.e. unbiased) state, the first plurality of radially flexible fingers 62 extend radially inwards of the second plurality of radially flexible fingers 64 (as shown in FIGS. 4 and 6). As shown in FIG. 6, the first plurality of radially flexible fingers 62 are alternately arranged with the second plurality of radially flexible fingers 64 around the circular configuration and the first and second plurality of radially flexible fingers 62,64 are defined by axial slots in the collet member 20. In the non-limiting embodiment shown in the Figures, the first plurality of radially flexible fingers 62 comprises three radially flexible fingers 62 and the second plurality of radially flexible fingers 64 comprises three radially flexible fingers 64. The first plurality of radially flexible fingers 62 each have a radially inwardly projecting lug 62a with a tapered profile whilst the second plurality of radially flexible fingers 64 each have a radially inwardly projecting lug 64a with a substantially square profile.

During assembly of the propellant source 26 in the collet member 20, the stem 48 is passed axially through the first and second plurality of flexible fingers 62,64. The first plurality of radially flexible fingers 62 engage the stem 48 with the lugs 62a locating in the groove 48a of the stem 48. However, due to the radial position of the second plurality of radially flexible fingers 64, the second plurality of radially flexible fingers 64 do not engage the stem 48 (as shown in FIG. 4). The engagement of the stem 48 by the first plurality of fingers 62 inhibits axial movement of the stem 48 relative to the collet member 20 when the stem 48 (or propellant container 26 more generally) is urged axially forward with a force up to a certain magnitude (i.e. a force threshold). However, given that the stem 48 is not engaged continuously about its entire circumference (due to the second plurality of radially flexible fingers 64 not engaging the stem 48), given that the lugs 62a of the first plurality of radially flexible fingers 62 each have a tapered profile, and given that the first plurality of radially flexible fingers 62 are radially flexible, there reaches a point at which the engagement of the first plurality of radially flexible fingers 62 is insufficient to prevent axial movement of the stem 48 relative to the collet member 20. That is, when the stem 48 is urged axially forwardly with a force substantially equal to or greater than the force threshold, the first plurality of radially flexible fingers 62 do not inhibit axial movement of the stem 48 relative to the collet member 20 such that the stem 48 is able to move relative to the collet member 20. In particular, the first plurality of radially flexible fingers 62 flex radially outward to permit the relative movement of the stem 48. The force threshold should be less than or substantially equal to the force required to compress the biasing member 56 and permit movement of the stem 48 relative to the reservoir housing 44. This way, in the configuration shown in FIG. 4 (i.e. in a partly assembled state), the propellant container 26 is retained in the collet member 20 to the extent that it will not fall out, however depression of the button 22 (or a force applied directly to the propellant container 26), deliberate or otherwise, will cause the first plurality of radially flexible fingers 62 to disengage the stem 48 and permit the stem 48 and the remainder of the propellant source 26 to move axially forwardly relative to the collet member 20 and not provide a reaction surface that would permit the stem 48 to move axially relative to the reservoir housing 44. Therefore, the first plurality of radially flexible fingers 62 retain the propellant source 26 in the collet member 20 but do not permit propellant to be dispensed from the propellant source 26 when in the partly assembled state shown in FIG. 4. Such a mechanism is particularly advantageous in preventing accidental dispensing of propellant during handling, storage and transportation of the sub-assembly 12. It should be noted that whilst the front housing 18 is absent from FIG. 4, the presence of the front housing 18 does not affect the selective engagement of the first plurality of radially flexible fingers 62 described above. Therefore the complete sub-assembly 12 will advantageously have a low risk of accidental discharge of propellant. Additionally or alternatively, the button 22 may be provided with a cover that prevents the button 22 being depressed. In such an embodiment, the cover would need to be removed, opened or disengaged prior to actuation of the device 10.

FIG. 5 shows the device 10 with the syringe 14 installed in the sub-assembly 12. As can be seen from FIG. 5, the presence of the syringe barrel 28 causes the second plurality of radially flexible fingers 64 to be biased radially inwardly and engage the stem 48. In particular, lugs 64a of the second plurality of radially flexible fingers 64 locate in the groove 48a of the stem 48. As described above, the lugs 64a have a substantially square (i.e. non-tapered) profile and this profile corresponds to the profile of the groove 48a thereby enhancing the engagement of the stem 48 by the second plurality of radially flexible fingers 64. With the syringe 14 installed in the sub-assembly 12, each of the first and second plurality of radially flexible fingers 62,64 are radially restrained between the syringe barrel 28 and the stem 48 such that radial flexing of the first and second plurality of radially flexible fingers 62,64 is substantially prevented. Therefore the lugs 62a,64a located in the groove 48a block the axial path of the stem 48 and prevent movement of the stem 48 relative to the collet member 20. In particular, movement of the stem 48 relative to the collet member 20 is prevented even when the stem 48 (or propellant source 26 generally) is urged axially forwardly with a force substantially equal to or greater than the force threshold and when urged axially forwardly with a force greater than the force required to compress the biasing member 56. Therefore, when the syringe 14 is installed in the sub-assembly 12, the first and second plurality of radially flexible fingers 62,64 provide a reaction surface that substantially prevents movement of the stem 48 such that the reservoir housing 44 may move relative to the stem 48 and permit the dispensing of propellant from the reservoir 46. Whilst FIG. 5 shows the barrel 28 itself providing a surface that causes the second plurality of radially flexible fingers 64 to be biased radially inwardly and engage the stem 48, in alternative embodiments another component may provide a surface that causes the second plurality of radially flexible fingers 64 to be biased radially inwardly and engage the stem 48 when the syringe 14 is installed in the sub-assembly 12. In one example, the barrel 28 may have a diameter that larger than a diameter defined by the second plurality of radially flexible fingers 64 to the extent that the barrel 28 does not cause the second plurality of radially flexible fingers 64 to be biased radially inwardly and engage the stem 48 when the second plurality of radially flexible fingers 64 are inserted into the barrel 28. In this example, there may be present a collar or other spacer component that is radially disposed between the barrel 28 and the second plurality of radially flexible fingers 64 and causes the second plurality of radially flexible fingers 64 to be biased radially inwardly and engage the stem 48. The sub-assembly 12 may therefore be used in a variety of differently sized syringes 14 provided a suitably dimensioned collar or spacer component is provided. Various components of the sub-assembly 12 may be suitably sized to receive a syringe of a particular diameter. For example, the front housing 18 and/or locking ring 24 may each be provided in a specific size to accommodate a syringe 14 of a particular size or particular range of sizes.

Figure 7:
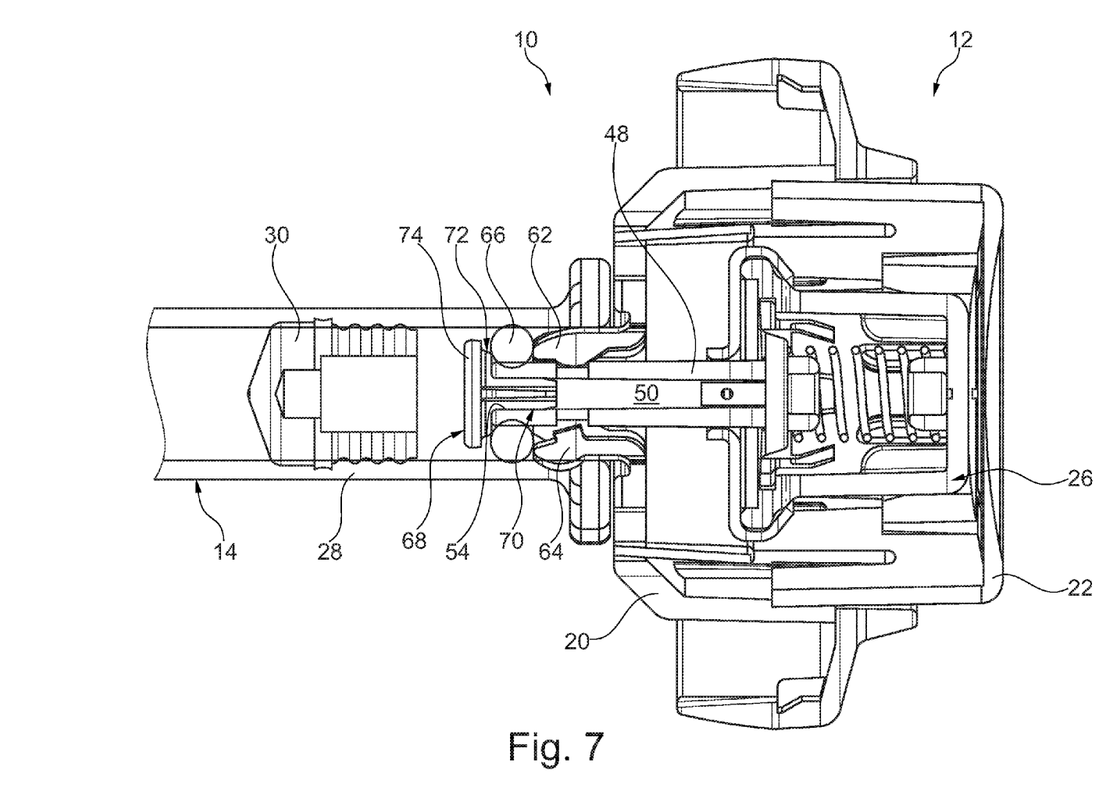
FIG. 7 is a cross-sectional view of a medicament delivery device without a front housing and a locking ring for clarity purposes.

FIG. 7 shows a cross-sectional view of the device 10 with the front housing 18 and locking ring 24 omitted for clarity purposes. As shown in FIG. 7, an O-ring seal 66 circumvents a forward end of the stem 48 and a retainer member 68 is disposed in the bore 50 of the stem 48 and passes through the open outlet end 54. The O-ring seal 66 seals the stem 48 to the syringe barrel 28 such that propellant provided to the syringe 14 by the propellant source 26 is substantially sealed between the stopper 30 and the O-ring seal 66.

Figure 8:
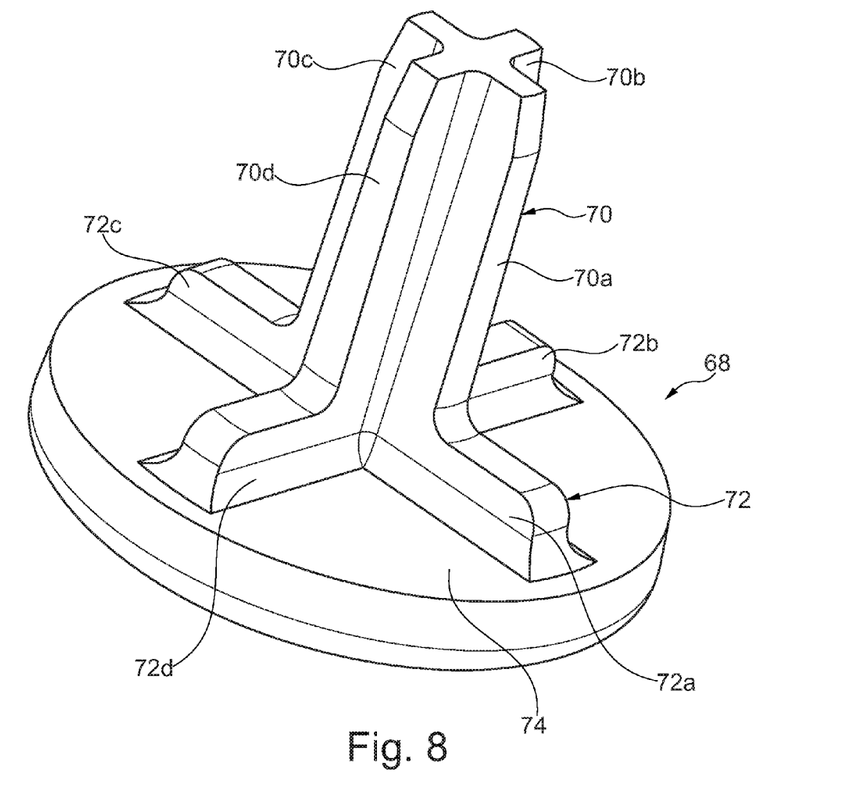
FIG. 8 is a perspective view of the retainer member of the device of FIG. 7.

The retainer member 68 is shown in more detail in FIG. 8 from which it can be seen to include a spigot 70 and a retainer flange 74 that extends radially outwardly from the spigot 70 by an amount greater than the diameter of the stem 48. In the embodiment shown in the Figures, the spigot 70 has a cross-shaped profile in a radial cross-section, being formed of four orthogonal limbs 70a,70b,70c,70d each extending radially outwardly and axially. The spigot 70 tapers radially inwardly in an axially rearward direction at an axially rearward end to facilitate insertion of the spigot 70 in the bore 50. The limbs 70a,70b,70c,70d are arranged such that adjacent limbs define channels therebetween. In order to form a frictional fit, the limbs 70a,70b,70c,70d extend radially by an amount that is slightly more than the internal diameter of the bore 50 whereby slight compression of the spigot 70 permits insertion of the spigot 70 in the bore 50.

The retainer member 68 additionally includes spacer elements 72 that limit the axial depth to which the spigot 70 may be inserted into the bore 50. In the embodiment shown in the Figures, the spacer elements 72 are formed by four elements 72a,72b,72c,72d that each extend along an axially rear surface of the retainer flange 74 from each of the four limbs 70a,70b,70c,70d by a radial amount greater than the radius of the bore 50. The channels defined between adjacent limbs 70a,70b,70c,70d continue between adjacent elements 72a,72b,72c,72d.

When the spigot 70 is inserted in the bore 50 of the stem 48, the spacer elements 72 limit the rearmost axial position of the retainer member 68 relative to the stem 48. The retainer flange 74 extends radially outwardly beyond the radial extent of the stem 48 such that the presence of the retainer flange 74 retains the O-ring seal 66 on the stem 48. In the embodiment shown in the Figures, the O-ring seal 66 is retained axially between the retainer flange 74 and the first and second plurality of radially flexible fingers 62,64 of the collet member 20. The presence of channels between adjacent limbs 70a,70b,70c,70d and elements 72a,72b,72c,72d mean that the retainer member 68 does not seal the bore 50 when the spigot 70 is inserted therein. Instead, the channels provide a fluid pathways from the bore 50 through the open outlet end 54. In the embodiment shown in the Figures, the channels each have an axial section (between adjacent limbs 70a,70b,70c,70d) and a radial section (along the rear surface of the retainer flange 74). The effect of this channel geometry causes the retainer member 68 to additionally act as a spray head for propellant passing through the bore 50 and out of the open outlet end 54. This spray head arrangement is particularly advantageous in combination with propellants that are dispensed from the propellant source 26 as a liquid and rely on the thermal energy of the surroundings to vaporize so as to provide a vapour pressure that is sufficient to cause axially forwardly movement of the stopper 30. In such embodiments, it is preferable to spread the liquid propellant over as large an area as possible so that a maximal amount of the surrounding thermal energy is absorbed by the liquid propellant. In particular, it may be preferable to spray the liquid propellant onto the walls of the syringe barrel 28 to maximize thermal absorption. Thermal absorption from the walls of the syringe barrel 28 will lead to more effective vaporizing of propellant compared with themel absorption from the stopper 30 which is often made of an elastomeric material and often includes a well-like structure on an axially rearfacing surface. In accordance with certain embodiments of the present invention, the spray head effect may be achieved by a component (i.e. a spray head member) attached to the stem 48 without necessarily retaining an O-ring seal 66 on the stem 48. In particular, the spray head effect is achieved by a component that diverts an axial flow of propellant so that its direction of flow has a radial component. The result of the spray head effect is that propellant is radially deflected beyond the radial extent of the spray head as it exits the open outlet. Such an effect is advantageous for spreading liquid propellant over a large area of a syringe 14 installed in the sub-assembly 12. The retainer member 68 described above with reference to the drawings is particularly preferable in certain embodiments since it provides the spray head effect, retains the O-ring seal 66 on the stem 48 and is sized and shaped to permit passage through the first plurality of radially flexible fingers 62 and the second plurality of radially flexible fingers 64 when during assembly when the spigot 70 of the retainer member 68 is located in the bore 50 of the stem 48.

In alternative embodiments, the spigot 70 and channels may be formed differently to the arrangement shown in the Figures. However, the retainer member 68 may still serve to retain the O-ring seal 66 on the stem 48 and permit fluid to flow from the bore 50 out through the open outlet end 54. In one example, the channels may pass through the retainer flange 74. In further or alternative embodiments, the retainer flange 74 may not be a continuous flange, but may be any suitable configuration that extends radially beyond the radius of the stem 48 and serves to retain the O-ring 66 thereon.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A sub-assembly of a medicament delivery device, the sub-assembly comprising:
    a propellant source having a reservoir housing defining a reservoir and a stem defining a bore therethrough, at least one inlet in fluid communication with the bore, and an open outlet end in fluid communication with the bore, the stem being moveable relative to the reservoir housing between a first position in which the at least one inlet is not in fluid communication with the reservoir and a second position in which the at least one inlet is in fluid communication with the reservoir, the propellant source further comprising a biasing member for biasing the stem towards the first position; and
    a collet member having a first plurality of radially flexible fingers and a second plurality of radially flexible fingers wherein the first plurality of radially flexible fingers extend radially inwards of the second plurality of radially flexible fingers when each of said first and second plurality of radially flexible fingers are unbiased;
    wherein the first plurality of radially flexible fingers are configured to engage the stem so as to inhibit axial movement of the stem relative to the collet member when the stem is urged in an axial direction with a force less than a force threshold but permit axial movement of the stem relative to the collet member when the stem is urged in an axial direction with a force greater than or equal to the force threshold, and the second plurality of radially flexible fingers do not prevent axial movement of the stem relative to the collet member when in a radially outward position but engage the stem when in a biased radially inward position so as to inhibit axial movement of the stem relative to the collet member including when the stem is urged in an axial direction with a force that is substantially equal to or greater than the force threshold and that is substantially equal to or greater than the force required to compress the biasing member and permit the stem to move to the second position relative to the reservoir housing, wherein the force threshold is substantially equal to or less than the force required to compress the biasing member.

2. The sub-assembly according to claim 1, wherein the first plurality of radially flexible fingers and the second plurality of radially flexible fingers are circularly arranged relative to one another.

3. The sub-assembly according to claim 2, wherein the first plurality of radially flexible fingers and the second plurality of radially flexible fingers are alternately arranged in the circular arrangement.

4. The sub-assembly according to claim 1, wherein the first plurality of radially flexible fingers comprises three radially flexible fingers and the second plurality of radially flexible fingers comprises three radially flexible fingers.

5. The sub-assembly according to claim 1, wherein each of the first plurality of radially flexible fingers and second plurality of radially flexible fingers includes a radially inwardly directed lug for engaging the stem.

6. The sub-assembly according to claim 5, wherein the lugs on each of the first plurality of radially flexible fingers are tapered in an axial direction.

7. The sub-assembly according to claim 5, wherein the stem includes a circumferential groove in an outer surface of the stem, and wherein the lugs of the first plurality of radially flexible fingers and the second plurality of radially flexible fingers are engageable in said groove, wherein the presence of the lugs in the groove axially blocks a part of the stem.

8. The sub-assembly according to claim 1, wherein the propellant source includes a latching mechanism that is configured to latch the stem in the second position.

9. The sub-assembly according to claim 8, wherein the latching mechanism includes latching members that are arranged to permit axially rearwardly movement of the stern relative to the reservoir housing, but substantially prevent forwardly axial movement of the stem relative to the reservoir housing when the stem is displaced relative to the reservoir housing by a predetermined distance.

10. The sub-assembly according to claim 9, wherein the stem includes a stem flange extending radially outwardly from the stem inside the reservoir housing, and wherein the predetermined distance is the distance required to position the stem flange axially rearwardly of the latching members such that abutment of the stem flange by the latching members prevents forwardly axial movement of the stem relative to the reservoir housing.

11. The sub-assembly according to claim 1 further comprising an O-ring seal circumventing the stein at an axial position that is forward of the first plurality of radially flexible fingers and the second plurality of radially flexible fingers, wherein the O-ring seal is configured to form a seal between the stem and a syringe barrel when a syringe is installed on the sub-assembly.

12. The sub-assembly according to claim 11, further comprising a retainer member axially forwardly of the O-ring seal and configured to axially restrain the O-ring seal on the stem between the retainer member and the first plurality of radially flexible fingers and the second plurality of radially flexible fingers.

13. The sub-assembly according to claim 1, further comprising a front housing attached to the collet member.

14. The sub-assembly according to claim 1 further comprising a button that is axially moveable relative to the collet member, wherein axially forwardly movement of the button causes an axially forwardly force to be applied to a propellant container.

15. The sub-assembly according to claim 1, wherein fhe reservoir contains a liquefied gas propellant.

16. The sub-assembly according to claim 1, wherein the reservoir contains a propellant that is or contains a hydrofluoroalkane (HFA).

17. The sub-assembly according to claim 16, wherein the propellant is or contains HFA134a.

18. The sub-assembly according to claim 1, further comprising a syringe installed in the sub-assembly, the syringe comprising a barrel, a stopper axially moveable in the barrel and an outlet at a front end of the barrel, wherein the barrel biases the second plurality of radially flexible fingers to the biased radially inward position so as to inhibit axial movement of the stem relative to the collet member.

* * * * *